United States Patent
Vija et al.

(10) Patent No.: US 9,202,294 B2
(45) Date of Patent: Dec. 1, 2015

(54) CLINICAL COLLABORATION AND MEDICAL COMPUTING FRAMEWORK

(71) Applicants: Alexander Hans Vija, Evanston, IL (US); Michal Cachovan, Nürnberg (DE); Jun Ma, Schaumburg, IL (US); Xinhong Ding, Buffalo Grove, IL (US)

(72) Inventors: Alexander Hans Vija, Evanston, IL (US); Michal Cachovan, Nürnberg (DE); Jun Ma, Schaumburg, IL (US); Xinhong Ding, Buffalo Grove, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 77 days.

(21) Appl. No.: 13/909,212

(22) Filed: Jun. 4, 2013

(65) Prior Publication Data
US 2013/0322722 A1 Dec. 5, 2013

Related U.S. Application Data

(60) Provisional application No. 61/655,074, filed on Jun. 4, 2012.

(51) Int. Cl.
*G06K 9/00* (2006.01)
*G06T 11/00* (2006.01)
*G06F 19/00* (2011.01)

(52) U.S. Cl.
CPC ............ *G06T 11/003* (2013.01); *G06F 19/321* (2013.01)

(58) Field of Classification Search
None
See application file for complete search history.

(56) References Cited

U.S. PATENT DOCUMENTS

| | | | |
|---|---|---|---|
| 2008/0181471 A1* | 7/2008 | Chung et al. | 382/128 |
| 2009/0112619 A1* | 4/2009 | Owens et al. | 705/2 |
| 2012/0096149 A1* | 4/2012 | Sunkara et al. | 709/224 |

OTHER PUBLICATIONS

Burdett, Neil, Jurgen Fripp, Pierrick Bourgeat, and Olivier Salvado. "MILXView: a medical imaging, analysis and visualization platform." In E-Health, pp. 177-186. Springer Berlin Heidelberg, 2010.*
Vija et al., A method for improving the efficiency of myocardial perfusion imaging using conventional SPECT and SPECT/CT imaging systems, IEEE, pp. 3433-3437 (2010).
Vija et al., Analysis of a SPECT OSEM Reconstruction Method with 3D Beam Modeling and Optional Attenuation Correction: Phantom Studies, IEEE, pp. 2662-2666 (2004).
Shepp et al., Maximum Likelihood Reconstruction for Emission Tomography, IEEE, pp. 113-122 (1982).
Zeintl et al., Quantitative Accuracy of Clinical 99mTc SPECT/CT Using Ordered-Subset Expectation Maximization with 3-Dimensional Resolution Recovery, Attenuation, and Scatter Correction, J. Nucl. Med., pp. 921-928 (2010).
Hudson, et al., Accelerated Image Reconstruction Using Ordered Subsets of Projection Data, IEEE, pp. 601-609 (1994).

* cited by examiner

*Primary Examiner* — Atiba O Fitzpatrick
(74) *Attorney, Agent, or Firm* — Peter Kendall

(57) ABSTRACT

A method of clinical collaboration between a clinical site and an analysis site includes receiving scan data from a scanner via a first reconstruction computer system at the clinical site, implementing a reconstruction procedure on the received scan data using a second reconstruction computer system at the analysis site and configured in accordance with a reconstruction configuration parameter, the analysis site being remote from the clinical site, and transmitting data indicative of the reconstruction configuration parameter to the first reconstruction computer system to configure the first reconstruction computer system in accordance with the reconstruction configuration parameter.

20 Claims, 7 Drawing Sheets

FIG. 5

CLINICAL COLLABORATION AND MEDICAL COMPUTING FRAMEWORK

CROSS-REFERENCE TO RELATED APPLICATION

This application claims the benefit of U.S. provisional application entitled "Clinical Collaboration and Medical Computing Framework," filed Jun. 4, 2012, and assigned Ser. No. 61/655,074, the entire disclosure of which is hereby incorporated by reference.

BACKGROUND

The present embodiments relate to medical imaging.

Nuclear medicine uses radiation emission to acquire images that show the function and/or physiology of organs, bones or tissues of the body. Radiopharmaceuticals are introduced into the body by injection or ingestion. The radiopharmaceuticals are attracted to specific organs, bones, or tissues of interest. The radiopharmaceuticals cause gamma photons to emanate from the body, which are then captured by detectors. One or more detectors are used to detect the emitted gamma photons, and the information collected from the detector(s) is processed to calculate the position of origin of the emitted photon from the source (i.e., the body organ or tissue under study). The interactions of the gamma photons with scintillation crystals of the detector(s) produce flashes of light captured by optical sensors of the detector(s). The accumulation of a large number of emitted gamma positions allows an image of the organ or tissue under study to be displayed.

In single photon emission computed tomography (SPECT), a collimator is placed in front a scintillation crystal to allow only gamma rays aligned with the holes of the collimator to pass through to the detector. The line along which the gamma emission occurred can thus be inferred. Mathematical procedures are used to solve the set of equations and reconstruct images from the raw scan data. Reconstruction methods may be non-iterative procedures (e.g., filtered back projection) or iterative procedures (e.g., maximum likelihood expectation maximization and minimization of an objective function).

Clinical studies are undertaken to determine the best reconstruction method, to determine parameters for new methods under development, or to improve the performance of existing reconstruction procedures. For example, clinical studies are directed to optimizing reconstruction procedures for imaging certain tissue regions or organs, such as the brain. Often, clinical studies are structured as collaborative efforts involving individuals at one or more clinical sites at which the scan data is collected, as well as individuals remotely located from the clinical sites. These collaborative efforts are time consuming to coordinate, making collection of information difficult.

SUMMARY

By way of introduction, the embodiments described below include systems and methods for facilitating clinical collaboration. Scan data, configuration parameter data, and/or other data may be shared between reconstruction computer systems at multiple collaboration sites, such as a clinical site and an analysis site.

In a first aspect, a method of clinical collaboration between a clinical site and an analysis site includes receiving scan data from a scanner via a first reconstruction computer system at the clinical site, implementing a reconstruction procedure on the received scan data using a second reconstruction computer system at the analysis site and configured in accordance with a reconstruction configuration parameter, the analysis site remote from the clinical site, and transmitting data indicative of the reconstruction configuration parameter to the first reconstruction computer system to configure the first reconstruction computer system in accordance with the reconstruction configuration parameter.

In a second aspect, a system to facilitate clinical collaboration with a clinical site includes a memory in which data transfer instructions and reconstruction instructions are stored, and a processor in communication with the memory and configured to execute the data transfer instructions to receive scan data from a scanner via a reconstruction computer system at the clinical site. The processor is configured to execute the reconstruction instructions to implement a reconstruction procedure on the received scan data in accordance with a reconstruction configuration parameter. The processor is further configured to execute the data transfer instructions to transmit data indicative of the reconstruction configuration parameter to the reconstruction computer system to configure the reconstruction computer system in accordance with the reconstruction configuration parameter.

In a third aspect, a computer program product to facilitate clinical collaboration between a clinical site and an analysis site includes one or more computer-readable storage media having stored thereon computer-executable instructions that, when executed by one or more processors of a computing system, cause the computing system to perform the method. The method includes anonymizing scan data captured by a scanner at the clinical site, transferring the anonymized scan data to a reconstruction computer system at the analysis site, and receiving a reconstruction configuration parameter from the reconstruction computer system to configure a reconstruction procedure.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 5 is a schematic view of an exemplary patient information interface generated by the reconstruction computer system of FIG. 2.

DETAILED DESCRIPTION OF THE PRESENTLY PREFERRED EMBODIMENTS

Figure 1:
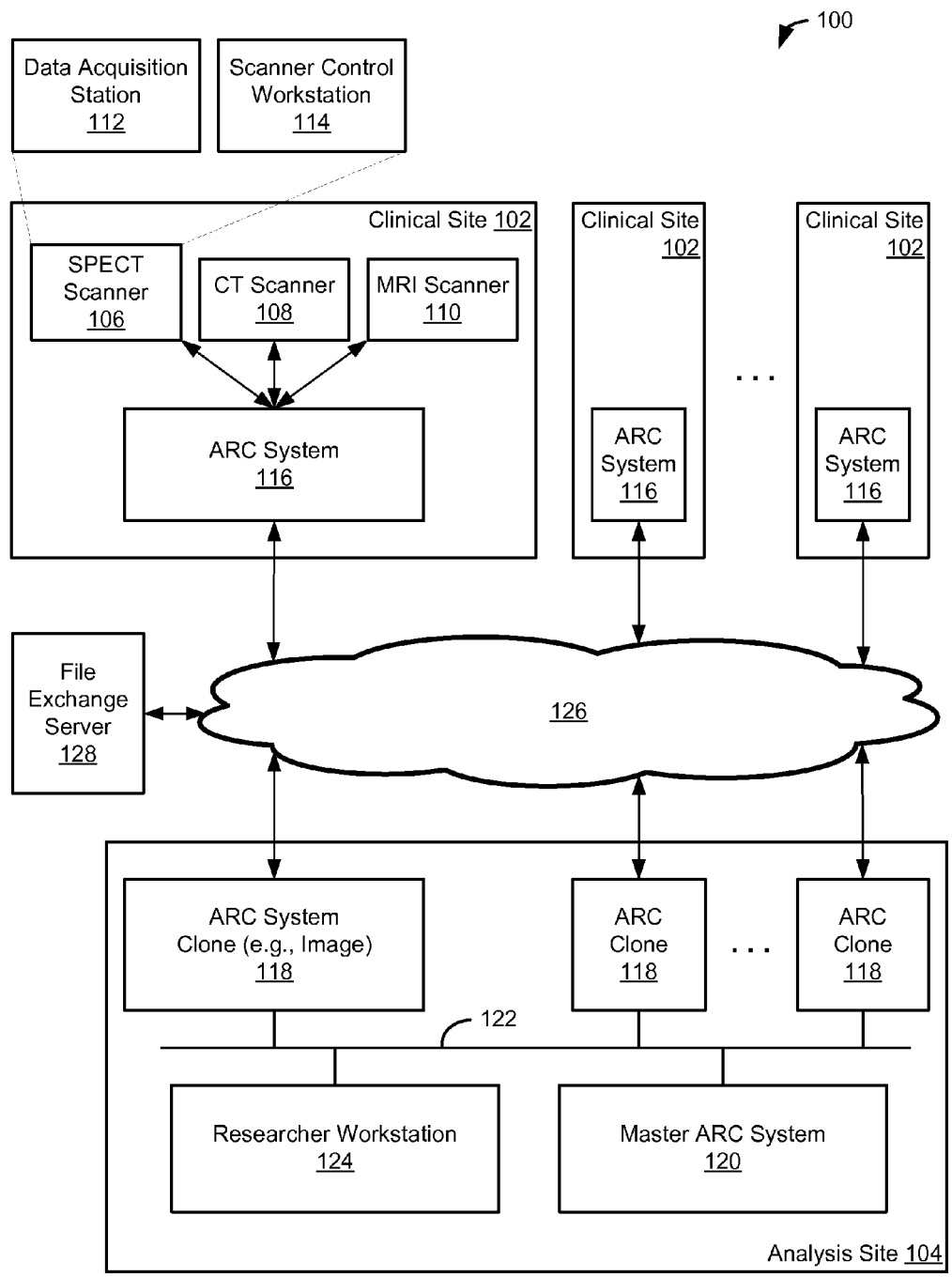
FIG. 1 is a block diagram of a clinical collaboration framework or networked computing infrastructure in accordance with one embodiment.

A framework facilitates clinical collaboration. The framework may be useful in clinical trials involving multiple parties. The framework may provide for the efficient transfer of data (e.g., scan data and/or software data) between the parties. The data transfers may be compliant with government regulations (e.g., HIPAA regulations). The framework may provide for remote access to equipment at a clinical site (e.g., for diagnostic and other work on such equipment). In some embodiments, the aggregation and processing of data from multiple data acquisition stations or sites (e.g., clinical sites) is supported. Alternatively or additionally, analysis sites are allowed to concurrently conduct multiple clinical trials. The disclosed framework may be used to support data acquisition, data transfer, reconstruction customization, physician/clinician review, reconstruction optimization, and/or data storage (e.g., result data storage). These and other features of the disclosed embodiments may help avoid scenarios where a collaboration partner is overwhelmed by large amounts of data.

The disclosed embodiments may be configured to automate various aspects of the clinical collaboration. As described below, scan data may be automatically anonymized, compressed, packaged, and/or otherwise processed for sharing with a collaboration partner, such as a service provider at an analysis site. The data may be shared with the collaboration partner to support the customization, configuration, implementation, and/or evaluation of one or more reconstruction procedures. Such automation may allow a single analysis site to support and otherwise participate in multiple clinical trials.

The automation of the clinical collaboration may be achieved through the replication of reconstruction computing resources at the sites involved in the collaboration. For example, the analysis site may include an image or clone of each reconstruction computer system at the clinical site(s) collaborating with the analysis site. Each clone computer system may be synchronized or otherwise configured to mirror a corresponding one of the reconstruction computer systems at the clinical site(s). Software, scan data, reconstruction configuration data, and/or other data may be synchronized or otherwise exchanged. The software may be configured to generate a reconstruction configuration interface presenting customization tools and a visualization interface for displaying multiple reconstruction results with an opportunity to provide feedback or comment on the results. The reconstruction configuration interface may present a reconstruction workbench for configuring and implementing reconstruction procedures.

In some embodiments, the synchronization and/or other aspects of the collaboration framework establish a real-time or live link between clinical and analysis sites. A real-time view of the clinical site may be provided at the analysis site, and vice versa. The reconstruction computer systems may be configured to share data concurrently with the implementation of other processing tasks, such as reconstruction tasks. The link may allow users to receive feedback or comments on the results of a reconstruction.

The disclosed embodiments are not limited to a particular imaging system modality. The disclosed framework may be applied in the context of hybrid imaging modalities, such as those that combine SPECT scanning with x-ray computed tomography (CT). Although described below in the context of a SPECT-CT hybrid modality system, other types of scanners may be used, including various types of nuclear imaging systems, such as positron emission tomography (PET). The disclosed framework is also not limited to use with a planning subsystem, or any particular type of planning subsystem. Scan data used for planning the scan(s) and/or rendering the scan data (and/or other purposes) may be acquired via a variety of different types of scanners (e.g., projection, emission, magnetic resonance, etc.). For example, the planning or support modality need not include a CT scanner, and may include or involve any now or hereafter developed imaging technology. The planning or support modality need not include or involve tomography.

FIG. 1 shows a framework 100 configured to facilitate image reconstruction collaboration. The framework 100 may include or be configured as a distributed or networked computing infrastructure through which the reconstruction collaboration is implemented. The framework 100 includes a number of sites collaborating on one or more clinical trials, other studies, research, or other work related to image reconstruction. Each site may correspond with a collaboration partner in which any number of users are involved in image reconstruction. The sites may be remotely located, e.g., having different geographic locations. In this example, the framework 100 includes three clinical sites 102 and an analysis site 104. The clinical sites 102 may be located at hospitals, clinics, or other medical service provider locations. Each clinical site 102 may be configured as, or affiliated with, a site of scanning equipment (i.e., a scanning site). The analysis site 104 may be located at a vendor or manufacturer of scanning equipment. The clinical sites 102 may be collaborating with the analysis site 104 on the same or different clinical trials. The framework 100 may include any number of clinical sites 102. The analysis site 104 may be distributed over multiple locations. For example, the analysis site 104 may include a network of computing resources distributed over multiple locations.

Each clinical site 102 includes one or more scanners. In this example, the clinical site 102 includes a SPECT scanner 106, a CT scanner 108, and a magnetic resonance imaging (MRI) scanner 110. The scanners may be any modality. The scanners 106, 108, 110 may be configured as a hybrid modality scanner or otherwise integrated to any desired extent. For example, the SPECT scanner 106 and the CT scanner 108 may be configured as a hybrid SPECT-CT system. Alternatively, one or more of the scanners 106, 108, 110 are discrete systems, and may be located in separate rooms. One or more of the scanners may be used for planning and/or image registration, although the clinical site 102 need not include a scanner used for planning or image registration. Additional, different, or fewer types of scanners may be used.

The SPECT scanner 106 is shown in greater detail. In this embodiment, the SPECT scanner 106 includes a data acquisition station 112 and a scanner control workstation 114 in communication with the data acquisition station 112. The data acquisition station 112 may include power supply and other equipment used to acquire scan data. The scanner control workstation 114 may be configured to control the operation of the data acquisition station 112 and process and/or view data collected by the data acquisition station 112. For example, in some cases, the scanner control workstation 114 may be configured to implement reconstruction procedures. The scanner control workstation 114 may alternatively or additionally be configured to generate one or more user interfaces directed to rendering images of the scan data collected by the image acquisition station 112. The scanner control workstation 114 may be shared by multiple scanners. For example, the scanner control workstation 114 may control the SPECT scanner 106 and the CT scanner 108 in a hybrid SPECT-CT system.

Each clinical site 102 includes a reconstruction computer system 116. The reconstruction computer system 116 may be directly or indirectly in communication with the scanners 106, 108, 110. The reconstruction computer system 116 may be provided to implement reconstruction procedures as part of the collaboration work (e.g., clinical study) of the framework 100. The reconstruction computer system 116 may thus be in addition to any typical clinical, diagnostic, archival, or other resources located at the clinical site 102 provided via, for example, the scanner control workstation(s) 114. The reconstruction computer system 116 and other components of the framework 100 may thus be disposed in a data flow (e.g., a research flow) in addition to the routine clinical and/or diagnostic data flows at the clinical site 102. Such routine data flows need not be affected by the framework 100.

The reconstruction computer system 116 may receive scan data from the scanners via the scanner control workstation(s) 114. In some cases, the reconstruction computer system 116 may utilize an archiving process of the scanner or scanner control workstation to obtain scan data from the scanners. The scan data may include listmode data, legacy data, raw data (e.g., raw CT data), and/or other types of scan data. In an alternative embodiment, the scanner control workstation 114 also implements the reconstruction computer system 116.

The reconstruction computer systems 116 may be referred to herein as advanced reconstruction computer (ARC) systems. The reconstruction procedures of the ARC systems 116 may be considered to provide advanced reconstruction functionality relative to the conventional reconstruction procedures implemented by the scanners. For example, the scanner control workstations 114 may also be configured to implement reconstruction procedures. Alternatively, the reconstruction computer system 116 receives scan data from the data acquisition stations 112 directly. Each clinical site 102 may include any number of ARC systems 116. In some cases, the ARC systems 116 are dual function computer systems, which may be used, e.g., for diagnostic and clinical purposes.

The framework 100 has an architecture that includes a respective reconstruction computer system, or ARC system clone 118, at the analysis site 104 to mirror or match the ARC system 116 of each clinical site 102. In this embodiment, the analysis site 104 includes a discrete computer system for each ARC system clone 118. In alternative embodiments, the ARC systems clones 118 may be configured as ARC clone images implemented on a common computer system. For example, the ARC system clones 118 may be implemented as virtual machines. Any number of physical computer systems may be used to implement the ARC system clones 118 of the analysis site 104.

The ARC systems 116 and the ARC system clones 118 may be configured with matching software instruction sets to support the reconstruction collaboration. As described below, the software instruction sets may include modules directed to implementing, configuring, and evaluating image reconstruction procedures. Scan and other data (e.g., data indicative of reconstruction configuration parameters established via the software instruction sets) may also be replicated or shared between the ARC systems 116 and the ARC system clones 118. Users at the clinical site 102 and the analysis site 104 may thus have the opportunity to implement and evaluate identically configured reconstruction procedures on the same scan data sets.

Each ARC system clone 118 may not be an exact replication of the corresponding ARC system 116 at the clinical site 102. In some embodiments, each ARC system 116 may include a number of utilities or tools that need not be present on the ARC system clones 118 or vice versa. For example, the ARC system 116 may include data transfer, handling, or processing tools, such as tools for receiving or otherwise obtaining scan data from the scanners.

The analysis site 104 may include a master ARC system 120 in communication with each ARC system clone 118. The master ARC system 120 may be configured to push software updates to the ARC system clones 118 over a network 122 of the analysis site 104. The software updates may then be passed along to the ARC systems 116 at the clinical sites 102. The master ARC system 120 may also be configured to integrate reconstruction tools and other software for deployment to the ARC system clones 118 and the ARC systems 116. One of the clones 118 may be or may implement the master ARC system 120.

The analysis site 104 may include one or more researcher workstations 124 in communication with each ARC system clone 118 via the network 122. Each researcher at the analysis site 104 may use a respective one of the researcher workstations 124. The researcher workstation 124 may be configured to generate a user interface directed to controlling one or more of the computing resources of the analysis site 104. For example, the researcher workstation 124 may be configured to initiate, implement, or coordinate the delivery of software updates from the master ARC system 120 to the ARC system clones 118. The researcher workstation 124 may be used to develop reconstruction tools and/or other software to be pushed to the master ARC system 120 and, in turn, to the ARC system clones 118 and the ARC systems 116. Alternatively or additionally, the researcher workstation 124 is configured to coordinate the processing or otherwise interact with the ARC system clones 118. The researcher workstation 124 may communicate with each ARC system clone 118 to obtain data for analysis, visualization, and other processing. For example, the researcher workstation 124 may be used to aggregate scan data from multiple ARC system clones 118. The aggregated scan data may then be processed in accordance with reconstruction procedures configured via an interface generated by the researcher workstation 124. In some cases, the researcher workstation 124 may be configured with the same software instruction sets used by the ARC systems 116 and the ARC system clones 118 for image reconstruction, reconstruction procedure configuration, and/or image reconstruction result evaluation. The researcher workstation 124 may be integrated with the master ARC system 120 and/or ARC system clones 118 to any desired extent.

The ARC systems 116 and the ARC system clones 118 may exchange software instruction and other data via a distributed network 126, such as the Internet. A two-way communication link may be established between each ARC system 116 and its corresponding ARC system clone 118. For example, software update data may be transferred from the ARC system clone 118 to the ARC system 116, while scan data may be transferred in the opposite direction. Reconstruction configuration, result, and feedback data may be transferred in either direction depending upon which site initially implements the reconstruction procedure. The two-way communication link over the distributed network 126 may be established in accordance with a variety of communication connections or techniques, such as a Virtual Private Network (VPN) connection.

Alternatively or additionally, the data exchanges may pass through or utilize a file exchange server 128 or other service available via the distributed network 126. The extent to which the data exchanges between the ARC systems 116 and the ARC system clones 118 are direct or indirect may thus vary.

In some embodiments, the communication link between one of the ARC systems 116 and the corresponding ARC system clone 118 is configured as a synchronization link. Updates to software instruction data, scan data, reconstruction parameter data, or other data at either the ARC system 116 or the ARC system clone 118 may thus be replicated at the other site. The synchronization link may establish a live or real-time link between the ARC system 116 and the ARC system clone 118. The data exchanges may thus be implemented concurrently with other data processing, as described below. The live link may allow users at the analysis site 104 to have a real-time view of the data and information collected or otherwise available at the clinical site 102. Conversely, the live link may allow users at the clinical site 102 to have a real-time view of the reconstruction configuration and result data generated or established at the analysis site 104.

In other embodiments, the transfer of data between the ARC system 116 and the ARC system clone 118 need not involve a network or other data transmission. For example, the transfer of scan data may be achieved via physical delivery of a CD, DVD, USB drive, or other storage device. In such cases, other types of data (e.g., reconstruction configuration parameters) may nonetheless be transmitted between the clinical site 102 and the analysis site 104. A non-real time or non-live link is used. Any combination of physical delivery and data transmission may be used.

Figure 2:
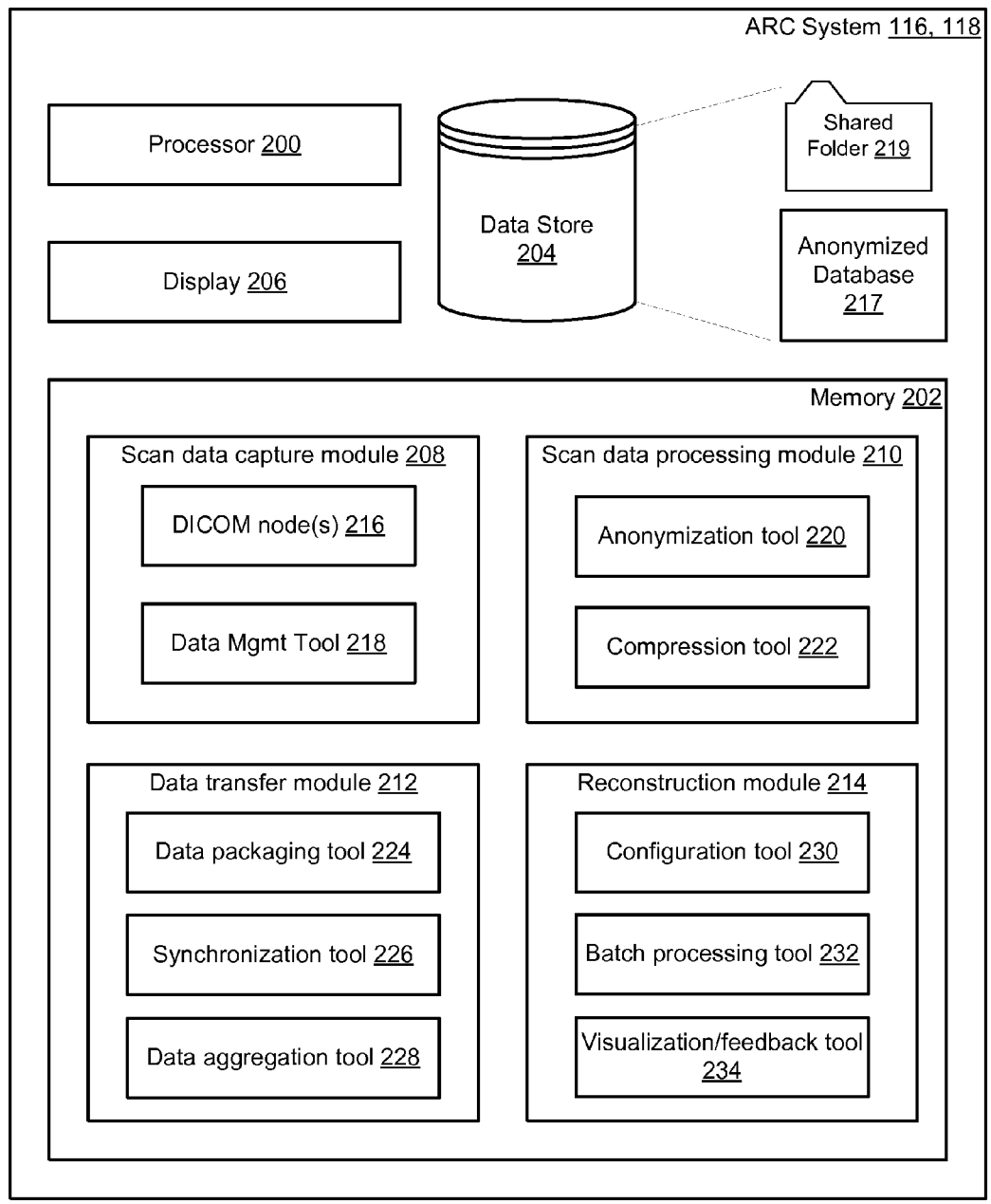
FIG. 2 is a block diagram of a reconstruction computer system of the framework of FIG. 1 in accordance with one embodiment.

FIG. 2 shows one of the ARC systems 116 (or one of the ARC system clones 118) in greater detail. The ARC system 116 includes a processor 200 and a memory 202 in which instructions configured for execution by the processor 200 are stored. The processor 200 is in communication with the memory 202 and configured to execute the instructions to implement various reconstruction tasks or methods. In this example, the ARC system 116 also includes a data store 204 for storage of data to be processed or generated by the processor 200, and a display 206 coupled to the processor 200 on which user interfaces and reconstructed images are displayed. The ARC system 116 may alternatively or additionally access or store data from a remote data store for either input or output data. In some embodiments, the ARC system 116 uses a display of the researcher workstation 124 (FIG. 1) or other computing system rather than include a separate display as shown.

The instructions stored in the memory 202 may configure the processor 200 to implement data transfer tasks and/or reconstruction tasks. The data transfer tasks may be directed to capturing, transferring, or otherwise obtaining or sharing scan or other data. The reconstruction tasks may be directed to configuration, processing, or evaluation of the reconstruction procedure. In this example, the instructions include a scan data capture module 208, a scan data processing module 210, a data transfer module 212, and a reconstruction module 214. The organization of the instructions into modules may vary from the example shown. Additional, fewer, or alternative modules may be provided. For example, the instructions of two or more of the modules (e.g., the scan data processing module 210 and the data transfer module 212) may be integrated to any desired extent. One or more of the modules or instruction sets thereof may be directed to tasks only performed at either the clinical site 102 or the analysis site 104. Some of the modules or instruction sets may thus be only present on the ARC systems 116 or the ARC system clones 118.

The scan data capture module 208 causes the processor 200 to receive or otherwise obtain scan data. For example, in the ARC system 116, the processor 200 may be configured by the scan data capture module 208 to obtain the scan data from a scanner. The scan data has not yet been anonymized. Alternatively, the scan data capture module 208 may configure the processor 200 of one of the ARC system clones 118 to obtain the scan data from the scanner via the corresponding ARC system 116 at the clinical site 102 (FIG. 1). The scan data capture module 208 may be configured to automatically or periodically obtain the scan data. For example, the scan data capture module 208 of one of the ARC systems 116 may be triggered to obtain the scan data as a result of detecting the presence of new scan data available at the scanner. With the ARC system clones 118, the scan data capture module 208 may be triggered by the initiation of the synchronization or other transmission of scan data by the corresponding ARC system 116. The scan data capture module 208 may be triggered in other ways, including, for instance, the arrival of the scan data.

The scan data capture module 208 may cause the processor to store the scan data in the data store 204 and/or the memory 202. Storage of the scan data may include the generation and storage of metadata indicative of one or more aspects of the scan data. One or more metafiles may be generated and stored in the data store 204. In some cases, the metadata may be used for indexing the scan data. In this embodiment, the scan data may be received via the Digital Imaging and Communications in Medicine (DICOM) standard. For example, the scan data capture module 208 may cause the processor 200 to present, provide, or establish one or more DICOM nodes 216 to support the data transmission. Upon receipt of the scan data via the DICOM node(s) 216, the scan data may then be anonymized as described below before storage in an anonymized database 217 or other data structure of the data store 204. For non-DICOM data, such as non-DICOM CT scan data, the scan data capture module 208 may include a data management tool 218 or other data storage tool to manage the receipt and/or storage of the non-DICOM data in one or more folders 219. For example, the data management tool 218 may be configured to define and/or establish a file structure, folder structure, database table, or other data storage structure, so that the scan data is stored in the ARC system 116 and the corresponding ARC system clone 118 in accordance with a common storage convention. The data management tool 218 may be configured to standardize the naming of folders and files, but any data storage structure may be used. The naming and storage conventions may be indicative of the clinical site, the clinical trial or other project, the analysis site, individual users at the analysis site, and/or other parameter. In some cases, each folder 219 may be configured as a shared folder to support data synchronization between the ARC system 116 and the ARC system clone 118. The data management tool 218 may also initiate and/or coordinate the anonymization of the non-DICOM data. The anonymized non-DICOM data may then be stored in the anonymized database 217.

The scan data processing module 210 may cause the processor 200 to preprocess the scan data before transfer to the ARC system clone 118 for subsequent reconstruction processing. For example, the scan data may be preprocessed before a synchronization operation. In this embodiment, the scan data processing module 210 includes an anonymization tool 220 and a compression tool 222. The anonymization tool 220 causes the processor 200 to remove or change personal data in the scan data. The anonymization tool 220 may be applied to the scan data automatically upon receipt via the scan data capture module 208. Anonymization may thus occur before transfer of the scan data to the analysis site 104 (FIG. 1). The manner in which the scan data is anonymized may vary. In some embodiments, the anonymization tool 220 provides a user with an opportunity to configure or customize the anonymization procedure. For example, a user may define or select the fields to be deleted, renamed, or otherwise modified by the procedure. The anonymization may be configured to comply with any applicable government regulations implicated by the transfer of the scan data outside of the clinical site 102 (FIG. 1). In some embodiments, the instructions for the anonymization tool 220 are present only in the ARC systems 116, as anonymization is not implemented by the ARC system clones 118.

The compression tool 220 causes the processor 200 to apply a data compression procedure to the scan data before transfer to the ARC system clone 118. Any compression may be used, such as lossless compression. The compression tool 220 may also be configured to decompress the scan data upon receipt at the ARC system clone 118. Other types of data may also be compressed via the compression tool 220. For example, data indicative of reconstruction configuration parameters, reconstruction result feedback, and software instructions may be compressed.

Additional, fewer, or alternative data preprocessing procedures may be implemented by the scan data processing module 210. For example, a data encryption tool may be provided.

The processor 200 executes the instructions of the data transfer module 212 to transmit data between the ARC system 116 and the corresponding ARC system clone 118. The data transfers cause the same data to be available to both the ARC system 116 and the ARC system clone 118. For example, one or more reconstruction configuration parameters established on the ARC system clone 118 may be transferred to the ARC system 116 to configure the ARC system 116 in accordance with the reconstruction configuration parameters. As a result, the ARC system 116 and the ARC system clone 118 may implement a commonly configured reconstruction procedure. Because the scan data is similarly shared between the ARC system 116 and the ARC system clone 118, the commonly configured reconstruction procedure may also be implemented on the same scan data. As described below, these data transfers of the reconstruction configuration parameter settings and scan data may be implemented via a data synchronization procedure. Synchronizing the parameter settings of the ARC systems of the clinical and analysis sites may be useful for facilitating the image reconstruction collaboration.

In the embodiment of FIG. 2, the data transfer module 212 includes a data packaging tool 224, a synchronization tool 226, and a data aggregation tool 228. As with the above-described modules, some of the tools may have different functionality depending on whether deployed in the ARC system 116 or the ARC system clone 118, or whether the data is being received or transmitted. For example, the ARC system 116 may use the data packaging tool 224 to retrieve scan data from the data store 204 and package the scan data for transmission to the ARC system clone 118. Later, the ARC system 116 may use the data packaging tool 224 to unpack other types of data received from the ARC system clone 118, such as reconstruction configuration data. The ARC system clone 118 may similarly use the data packaging tool 224 to support such transmissions.

The synchronization tool 226 may cause the processor 200 to implement a data synchronization procedure. The synchronization procedure may be automatically triggered. For example, the synchronization tool 226 may cause the processor 200 to detect a change to a data structure in the data store 204, such as a new scan data set or a change in reconstruction configuration parameter settings. Upon detecting the new data or change, the synchronization tool 226 may initiate a data transfer to the ARC system 116 (if transferring from the analysis site 104 to the clinical site 102) or the ARC system clone 118 (if transferring from the clinical site 102 to the analysis site 104). The synchronization tool 226 may periodically check the data store 104 or other memory to detect the new data or changes. The frequency may be set to a level to ensure that data synchronization occurs rapidly enough for a live or real-time link to be established.

The instructions for the data aggregation tool 228 may cause the processor 200 to aggregate scan data from the ARC systems 116 at multiple clinical sites. The scan data may be aggregated after an initial synchronization of scan data between one of the ARC systems 116 and its corresponding ARC system clone 118. The data aggregation tool 228 of the ARC system clone 118 may then deliver the scan data to another one of the ARC system clones 118 via the network 122 (FIG. 1). Such aggregation may allow scan data to be shared between clinical and/or analysis sites.

The reconstruction module 214 includes instructions for configuring, implementing, and evaluating a reconstruction procedure. The processor 200 is configured to execute the instructions of the reconstruction module 214 to implement a reconstruction procedure in accordance with one or more reconstruction configuration parameters. In this embodiment, the reconstruction module 214 includes instructions for a reconstruction configuration tool 230, a batch processing tool 232, and a visualization tool 234. The reconstruction module 214 may cause the processor 200 to generate one or more user interfaces to support and provide the functionality of one or more of the tools 230, 232, 234. The functionality may be integrated to any desired extent. For example, the functionality of the reconstruction configuration tool 230 together in a common user interface. Alternatively or additionally, interaction with the user interface for the reconstruction configuration tool 230 and/or the batch processing tool 232 may lead to the generation of a user interface for the visualization tool 234.

The reconstruction configuration tool 230 generates a reconstruction configuration interface that provides an opportunity to configure the reconstruction procedure to be applied to the scan data. Any number of configuration parameter settings may be established. The configuration may include the selection of parameter values or other settings and/or the identification of which parameters are to be set. The reconstruction configuration tool 234 may provide default values or other settings for certain parameters. The reconstruction configuration tool 234 may allow multiple reconstruction procedures to be configured.

The multiple reconstruction procedures may be implemented in a batch process through execution of the instructions of the batch processing tool 232. A user may be provided the option to select a number of reconstruction procedures to be implemented in a batch, or collectively. The multiple reconstruction procedures may include processing the scan data (e.g., of a single data set) in accordance with multiple sets of reconstruction parameter settings, and/or processing multiple scan data sets with the same or different reconstruction configuration parameter settings.

The batch processing tool 232 may be useful when a large number of data sets may be available for processing. For example, a large number of data sets may be available after the data from multiple clinical sites is aggregated by the analysis site 104 (FIG. 1). A large number of combinations of different scan data sets and varying configuration parameter settings may be efficiently processed and analyzed via such batch processing.

The processor 200 is further configured to execute the instructions for the visualization tool 234 of the reconstruction module 214 to generate a visualization interface. The visualization tool 234 may be directed to facilitating comparison of more than two reconstruction results and storage of feedback data for the comparison. For example, the results of the three image reconstructions may be presented via the visualization interface. The visualization interface may include a number of input panels or other user interface elements to collect comments and other feedback on the image reconstructions. In some cases, the collection of feedback may include the presentation of a number of questions via the visualization interface. The questions may seek comments from the user regarding the quality of the image reconstructions. For example, one question may ask whether the user prefers a first image over a second image, and then whether the user prefers the first image (or the second image) over a third image. Data indicative of a ranking of image quality may then be stored.

In the embodiment of FIG. 2, the ARC systems 116, 118 provide both data processing and user interface functions. The data processing and user interface functions may be provided separately in other embodiments. For example, at the analysis site 104 (FIG. 1), image reconstruction and other processing of the scan data may be implemented by the ARC system 116, while user interfaces are generated by the researcher workstation 124 (FIG. 1) or other computing system. Any number or type of operator consoles may be provided to implement the functionality of the configuration tool 230, the batch processing tool 232, the visualization tool 234, or other component or aspect of the reconstruction module 214.

In some embodiments, the scanning operation of one or more of the scanners 106, 108, 110 (FIG. 1) may be controlled and supported via the ARC system 116 and/or the ARC system clone 118. For example, the ARC system clone 118 may direct a corresponding one of the ARC systems 116 at the clinical site 102 (FIG. 1) to obtain further scan data of a subject.

The reconstruction module 214 may include instructions directed to incorporating scan data provided by the CT scanner 108 (FIG. 1) or other scanners into the reconstruction procedure. For example, the scan data from the CT scanner 108 may be used during image reconstruction as an overlay, for image registration, for attenuation correction, and/or for other purposes.

The processor 200 is or includes a general processor, digital signal processor, graphics processing unit, application specific integrated circuit, field programmable gate array, digital circuit, combinations thereof, or other now known or later developed device for processing emission information. The processor 200 is a single device, a plurality of devices, or a network of processors. For more than one device, parallel or sequential division of processing may be used. Different devices making up the processor 200 may perform different functions, such as one processor for filtering and/or subtracting raw data or reconstructed images. The processor 200 may include an application specific integrated circuit or field programmable gate array for performing various operations, such as iterative reconstruction. The processor 200 may be a processor of a workstation or other computer, or correspond with a portion of a processor of a workstation or other computer (e.g., when the ARC system 116, 118 is implemented as a virtual machine).

The processor 200 operates pursuant to stored instructions to perform various acts described herein. For example, the processor 200 may be operable to implement iterative reconstructions from one or more collections of data. The processor 200 may be configured by code or instructions sets stored on the memory 202 or other memory, by firmware, and/or by hardware to perform any or all of the acts described herein.

The memory 202 or the data store 204 is a buffer, cache, RAM, removable media, hard drive, magnetic, optical, database, or other now known or later developed memory. The memory 202 or the data store 204 is a single device or group of multiple devices. The memory 202 or the data store 204 is shown within the ARC system 116, 118, but may be outside or remote from other components of the ARC system 116, 118, such as an external database or PACS memory.

The memory 202 or the data store 204 may store data at different stages of processing. For example, the memory 202 may store raw data representing detected events without further processing, filtered or thresholded data prior to reconstruction, reconstructed data, filtered reconstruction data, an image to be displayed, an already displayed image, or other data. The memory 202 or the data store 204 (or a different memory) may store data used for processing, such as storing the data after one or more iterations and prior to a final iteration in reconstruction. For processing, the data bypasses the memory 202, is temporarily stored in the memory 202, or is loaded from the memory 202.

The memory 202 is additionally or alternatively a non-transitory computer readable storage medium storing processing instructions. For example, the memory 202 stores data representing instructions executable by the programmed processor 200 for reconstructing a positron emission tomography image for dynamic study and/or reconstructing an image in emission tomography. The instructions for implementing the processes, methods and/or techniques discussed herein are provided on non-transitory computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software stored or otherwise embodied on a computer-readable memory, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 206 is a CRT, LCD, plasma screen, projector, printer, or other output device for showing images generated by the ARC system 116, 118. The display 206 may be used to display a user interface for controlling the ARC system 116 and/or ARC system clone 118. The above-described scanners may have a separate display or user interface for control thereof. The display 206 may alternatively or additionally be used to display the images generated by the disclosed systems and methods. Such images may include separately rendered or reconstructed images from respective SPECT detectors.

The ARC systems 116, 118 described herein may include any number of processors, memories, and/or other digital circuitry to support implementation of the reconstruction-related tasks. Additional or alternative analog or digital control circuits may be used.

Figure 3:
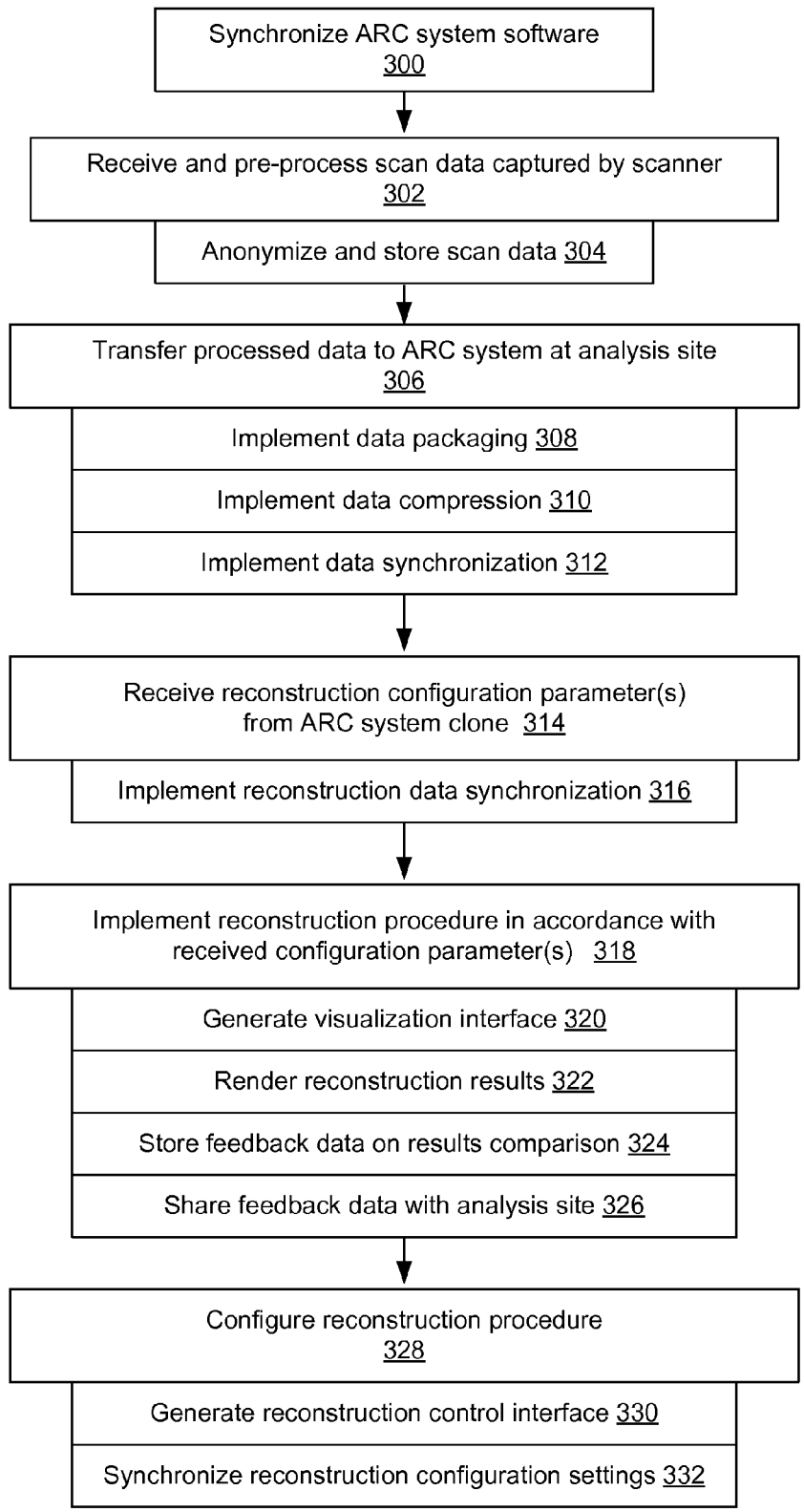
FIG. 3 is a flow diagram of a method of image reconstruction collaboration implemented by the reconstruction computer system of FIG. 2 at a clinical site in accordance with one embodiment.

FIG. 3 shows one embodiment of a method of image reconstruction collaboration between a clinical site and an analysis site, such as the clinical and analysis sites 102, 104 described above. The method is performed by one of the ARC systems 116 at the clinical site 102 or other data processing circuitry, such as a computer or workstation at one of the clinical sites 102. The method is performed in the order shown, but other orders may be used. For example, a reconstruction procedure may be implemented before receipt of parameter settings from the analysis site. Additional, fewer, or alternative acts may be implemented. For example, the method may include one or more additional acts directed to synchronization, such as transmitting data to the analysis site to determine whether synchronization is warranted.

The method may begin in an act 300 in which ARC system software is synchronized. The reconstruction module and other instructions of the ARC system may be synchronized with the instructions in the corresponding ARC system clone at the analysis site. Any software updates provided by the master ARC system 120 (FIG. 1) to the ARC system clones are thus passed along to the ARC systems at each clinical site.

In an act 302, scan data is received from one or more scanners. The scan data may be pre-processed for various purposes. For example, the scan data from multiple scanners may be processed for image registration. In other cases, image registration and/or other pre-processing is implemented at the scanner (e.g., by a scanner control workstation).

In this embodiment, the pre-processing includes anonymization of the scan data in an act 304. The anonymization may address government regulations, such as those arising from the privacy and security rules of the Health Insurance Portability and Accountability Act (HIPAA). To maintain the privacy of the scan subjects, the scan data is anonymized at the clinical site before transfer to the ARC system clone at the analysis site. The anonymization may include removal of personal information, modification of personal information, or a combination thereof. The act 304 may include the storage of the anonymized data in a database or other data structure.

The anonymized scan data is transferred in an act 306 to a reconstruction computer system at the analysis site, such as one of the ARC system clones described above. The data transfer may include the implementation of one or more data packaging procedures in an act 308, a data compression procedure in an act 310, and/or a data synchronization procedure 312. As described above, the anonymized scan data available for image reconstruction may be synchronized between the ARC system and its corresponding ARC system clone at the analysis site. The synchronization procedure may be triggered automatically upon the receipt of the scan data, storage of the anonymized data, or other act or event (e.g., involving the scan data).

One or more reconstruction configuration parameters are received in an act 314 from the reconstruction computer system to which the scan data is transferred in the act 306. For example, the reconstruction configuration parameter(s) may be received from the ARC system clone corresponding with the ARC system being configured. In the embodiment of FIG. 3, the receipt of reconstruction configuration parameter(s) is achieved in an act 316 during the implementation of a reconstruction data synchronization. The reconstruction data synchronization may also be configured to share scan data between the clinical and analysis sites. The acts 314 and 316 may thus be implemented concurrently or otherwise in conjunction with the scan data synchronization of the act 312. Alternatively or additionally, the reconstruction data synchronization may occur after one or more image reconstruction procedures are implemented at the analysis site. The image reconstruction procedures are implemented to test reconstruction configuration parameter settings to be proposed to the clinical site.

The received reconstruction configuration parameter(s) may be used to configure one or more reconstruction procedures. The ARC system implements a reconstruction procedure in an act 318 in accordance with the received reconstruction configuration parameter(s). In the embodiment of FIG. 3, a visualization interface is generated by the ARC system in an act 320. The results of the reconstruction procedure are rendered in an act 322. The visualization interface may present the reconstruction results with an opportunity for a user to enter comments and other feedback on the reconstruction results. In some embodiments, the visualization interface is configured to facilitate comparison of more than two reconstruction results. Data indicative of the comparison or other feedback is stored in an act 324. For example, the feedback data may be stored in a database or other data structure in the data store 204 (FIG. 2). The feedback data may also be shared in an act 326 with the analysis site. For example, the storage of the feedback data may trigger another synchronization operation with the corresponding ARC system clone.

The operator of the ARC system may also initiate the configuration of a reconstruction procedure. In this embodiment, a reconstruction procedure is configured in an act 328. The configuration at the clinical site may precede or be contemporaneous with configuration tasks at the analysis site. In some cases, the configuration may include configuring the previously implemented reconstruction procedure with a further reconstruction configuration parameter. The configuration may alternatively or additionally include adding or removing configuration parameters. The configuration parameter(s) may be changed, added, or removed via a reconstruction customization tool provided via a reconstruction control interface generated in an act 330.

Once the configuration parameter settings have been changed, data indicative of the parameter settings may be transferred in an act 332 to another reconstruction computer system, such as the corresponding ARC system clone. The data transfer may occur in another data synchronization procedure.

Figure 4:
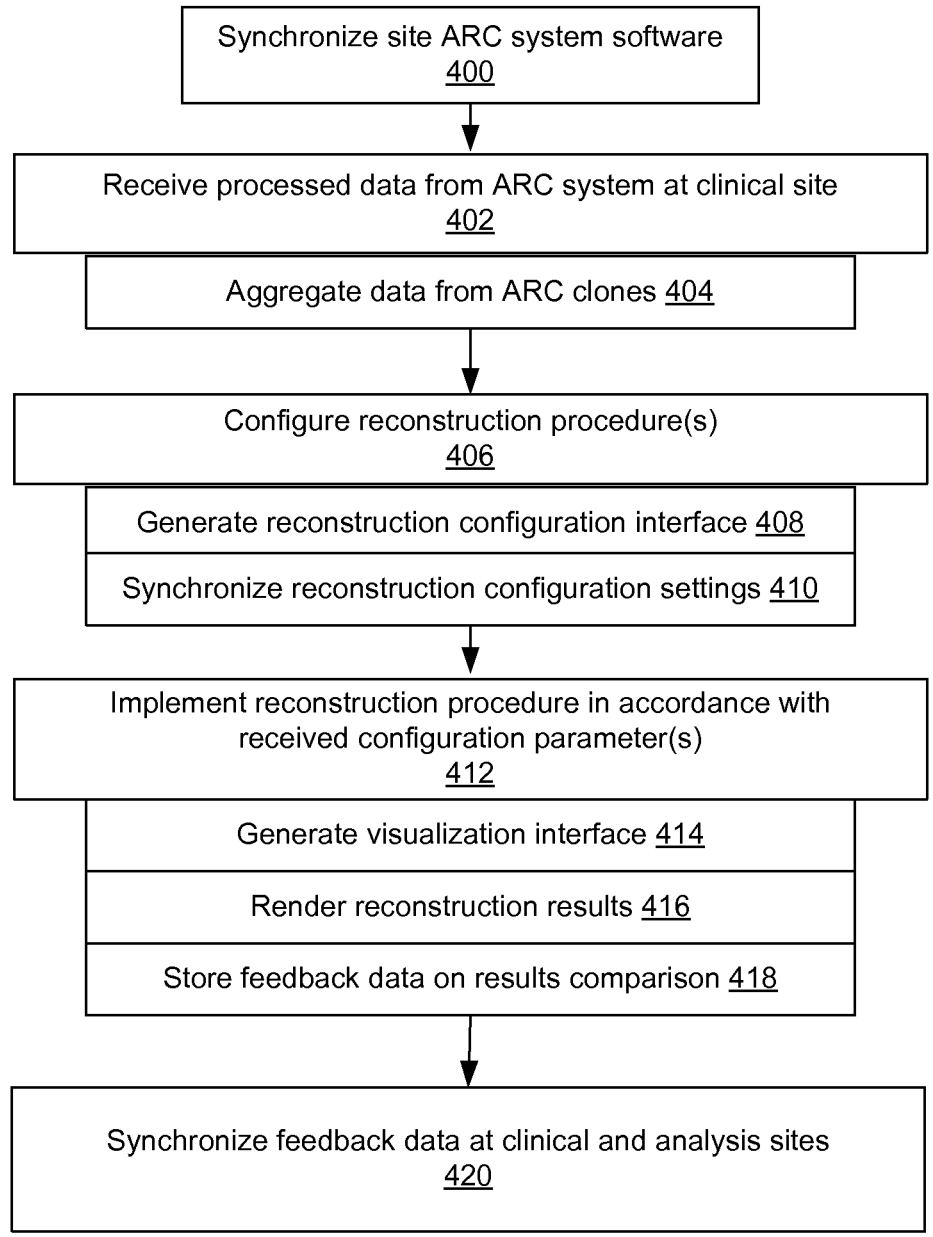
FIG. 4 is a flow diagram of a method of clinical collaboration implemented by the reconstruction computer system of FIG. 2 at an analysis site in accordance with one embodiment.

FIG. 4 shows the acts implemented at the analysis site during implementation of a method of image reconstruction collaboration in accordance with one embodiment. The method is performed by one of the ARC system clones 118 (FIG. 1) at the analysis site 104 (FIG. 1) and/or other data processing circuitry, such as a computer or workstation at the analysis site. The method is performed in the order shown, but other orders may be used. For example, ARC system software may be synchronized at any time during the method. Additional, fewer, or alternative acts may be implemented. For example, the method may include one or more additional acts directed to synchronization of reconstruction configuration parameter settings originating from the corresponding ARC system at the clinical site.

The method may begin in an act 400 in which ARC system software is synchronized. For example, the reconstruction module and other instructions of the ARC system clone may be synchronized with the instructions in the master ARC system 120 (FIG. 1). Such instructions may then be shared with the corresponding ARC system at the clinical site.

Scan data is received in an act 402 from the corresponding ARC system at the clinical site. The scan data is originally generated by a scanner with which the ARC system is in communication. The scan data may be anonymized as described above prior to the transfer. The scan data may be received via a data synchronization as described above. In the embodiment of FIG. 4, receipt of the scan data includes aggregating in an act 404 scan data from multiple ARC systems or other reconstruction computer systems not disposed at the analysis site.

In an act 406, one or more reconstruction procedures are configured. A reconstruction configuration interface may be generated in an act 408 at the ARC system clone. A number of configuration or customization tools may be presented via the interface. The tools may be used to add, remove, or otherwise modify various reconstruction parameter settings. Data indicative of the reconstruction configuration parameter(s) (e.g., the modifications thereto) may then be transferred or transmitted in an act 410 to the corresponding ARC system at the clinical site for configuration thereof in accordance with the reconstruction configuration parameter(s). The transfer or transmission of such data may include a data synchronization procedure, as described above.

Once the reconstruction procedure is configured in accordance with one or more reconstruction configuration parameters, the ARC system clone may then implement the reconstruction procedure in an act 412 on the received scan data. Multiple reconstruction procedures may be configured. Implementation of the reconstruction procedure(s) may include batch processing of the multiple reconstruction procedures. Multiple scan data sets may be batch processed. Alternatively or additionally, scan data may be batch processed in accordance with multiple sets of reconstruction parameters. In some cases, the synchronization or other transfer or transmission of the data indicative of the reconstruction configuration parameter(s) is implemented concurrently with the implementation of the reconstruction procedure. The reconstruction configuration parameter settings may thus be updated in real-time via, e.g., a live link, as described above.

Implementation of the reconstruction procedure may include generating in an act 414 a visualization interface, as described above. An image generated by each reconstruction procedure may be rendered in an act 416 via, for example, the visualization interface. The visualization interface may be configured to facilitate comparison of more than two reconstruction results and/or entry of other types of feedback regarding the reconstruction results. The visualization interface may also facilitate the storage in an act 418 of the feedback data.

In an act 420, feedback data is shared between the ARC system and the ARC system clone. The feedback data may be transferred from the ARC system to the ARC system clone, and/or vice versa, depending on the location of the user entering the comments or other feedback. The sharing or transfer may be implemented as part of a synchronization operation, as described above.

Figure 5:
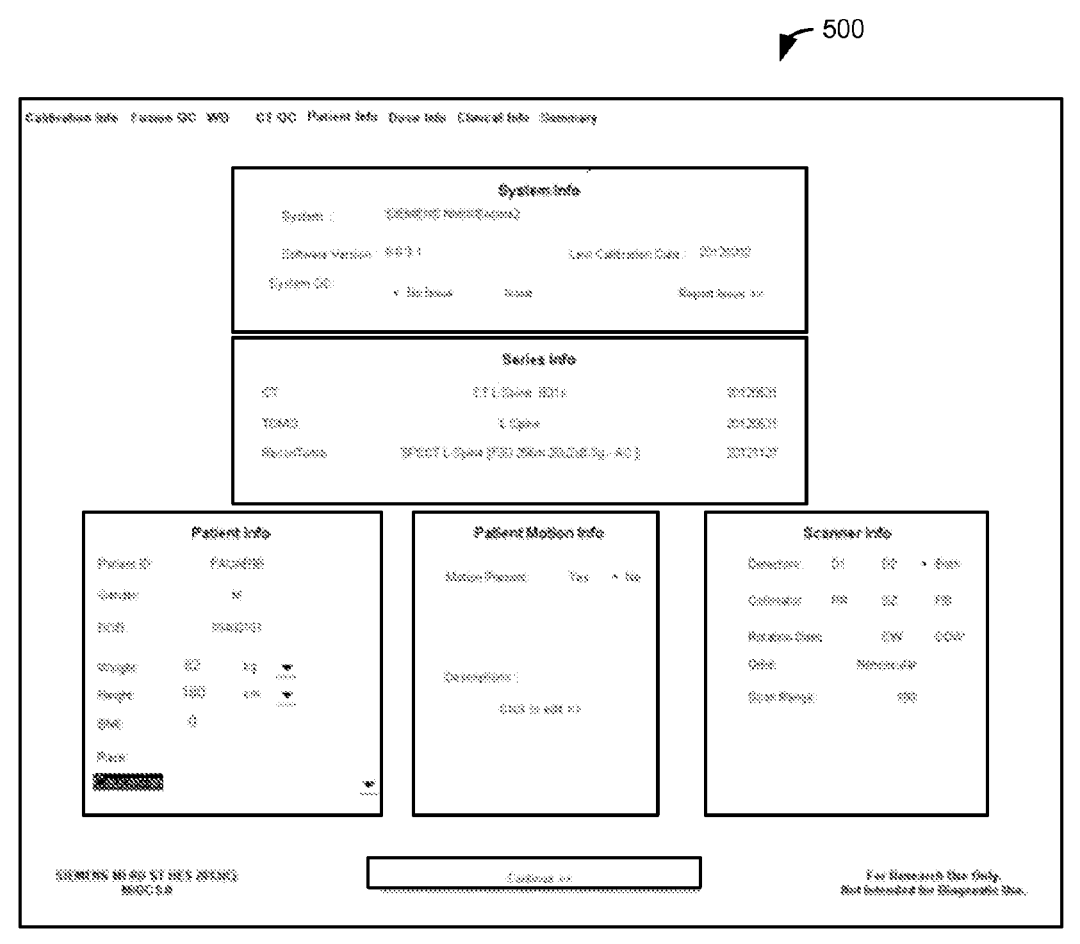

FIG. 5 depicts an exemplary screenshot of a patient information interface 500 generated by the above-described reconstruction computer systems, such as one of the ARC systems or ARC system clones. The patient information interface includes panes for entry and/or display of various types of information, including, for instance, information regarding the scanner (e.g., system, scan procedure, and other configuration details), the patient (e.g., height, weight, and other attributes not captured by scanner), and whether patient motion occurred during the scan. In this embodiment, the patient information interface includes additional display screens for collecting additional information, including, for instance, clinical information and other patient attributes, and comments or feedback on the quality of the image reconstruction. The patient information interface may be generated separately or in conjunction with the above-described reconstruction configuration and visualization tools. The patient information interface may be integrated with the reconstruction configuration and/or visualization interfaces to any desired extent. Additional, different, or fewer panes or types of information may be provided.

Figure 6:
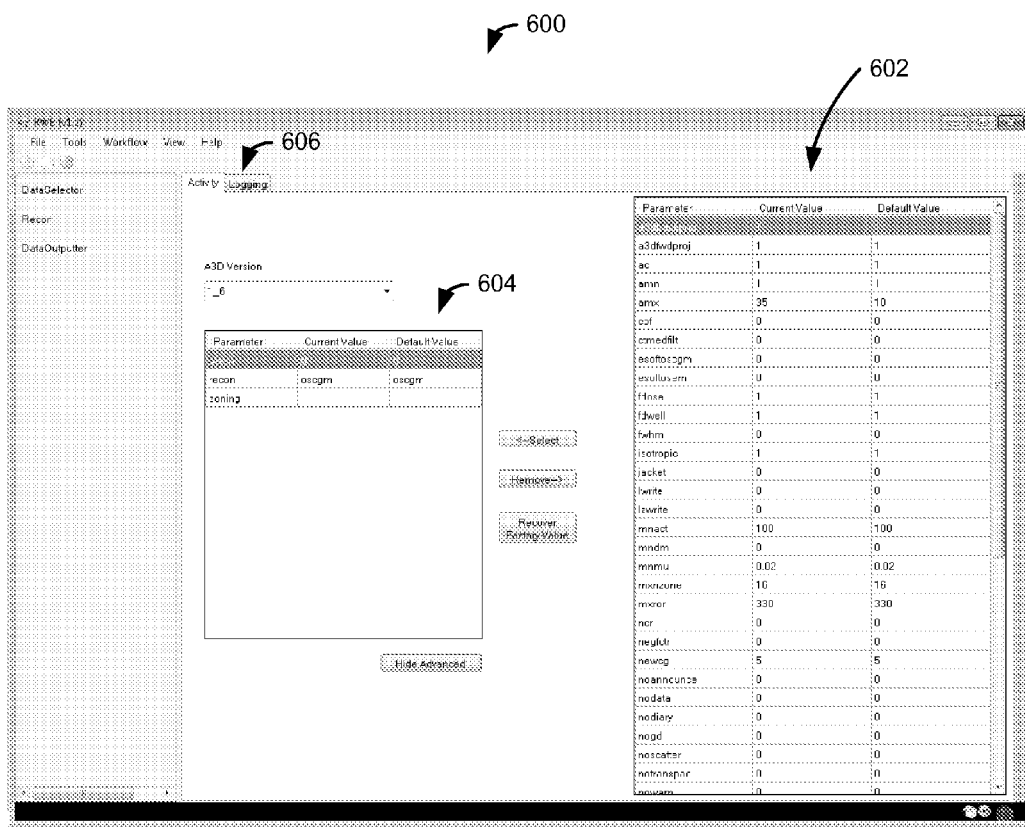
FIG. 6 is a schematic view of an exemplary reconstruction configuration interface generated by the reconstruction computer system of FIG. 2.

FIG. 6 depicts an exemplary screenshot of a reconstruction configuration interface 600 generated by the above-described reconstruction computer systems, such as one of the ARC systems or ARC system clones. The reconstruction configuration interface may be accessed or otherwise integrated with the above-described visualization interfaces. The reconstruction configuration interface 600 may present a reconstruction workbench having various tools, including a data selector tool, a reconstruction configuration tool, and a data output tool. In this embodiment, the reconstruction configuration interface includes a navigation pane that presents options to select the various tools. The data selector tool provides a user with an opportunity to select one or more scan data sets for processing. Upon selection of the data selector tool, the scan data sets available for processing may be listed via anonymized or other data. The reconstruction configuration tool provides a user with an opportunity to select one or more reconstruction configuration parameters for customization. As shown in FIG. 6, each parameter selected for customization is displayed in a table 602 identifying a current value and a default value. In this example, parameters of interest are selected for display in a separate table 604. Elements of the tables 602, 604 may be selected for modification. The data output tool provides a user with an opportunity to view the results of an image reconstruction.

The reconstruction configuration tool portion of the interface 600 includes a logging tab 606 to display status information regarding an ongoing reconstruction procedure. The status information may include or be presented as a log of system messages or other status data. For example, the log may identify which iteration of the reconstruction procedure is currently running.

Figure 7:
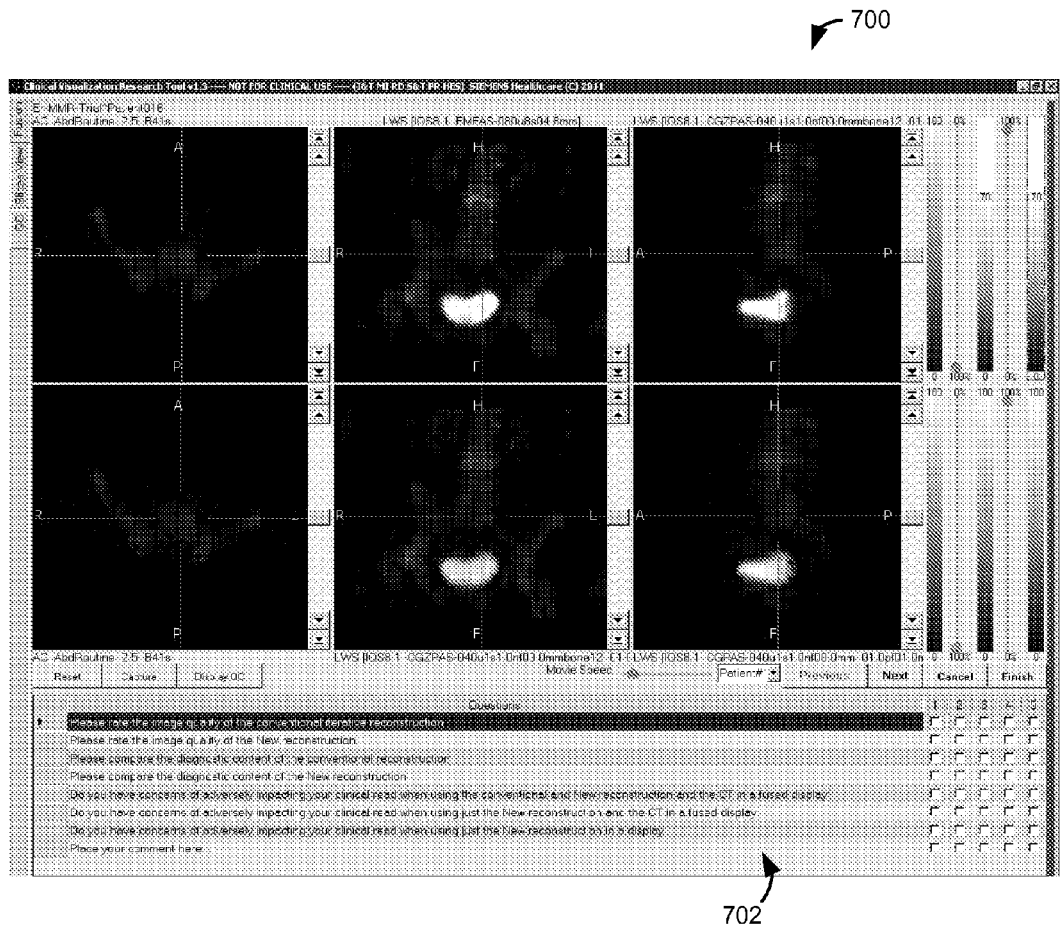
FIG. 7 is a schematic view of an exemplary visualization interface generated by the reconstruction computer system of FIG. 2.

FIG. 7 depicts an exemplary screenshot of a visualization interface 700. A number of visualization tools may be made available via the interface 700, for example, after the implementation of a reconstruction procedure. The visualization interface 700 may be integrated with any one or more of the above-described interfaces to any desired extent. The visualization interface 700 provides different viewing options for the image reconstruction, including, for instance, a slice view and a view fusing scan data from multiple modalities (e.g., a fusion view of, for instance, SPECT scan data with a CT scan data overlay). A number of user interface control elements are made available. In this example, the control elements are configured for selecting a scan data set (e.g., patient 1, patient 2, etc.), modifying the color, contrast, and other aspects of the view, and for displaying a movie or other time sequence of the scan data.

The visualization interface 700 includes a feedback pane 702 configured to collect feedback data regarding the image reconstruction. In this embodiment, the feedback pane 702 presents a number of questions and/or statements with an opportunity for a user to enter a response, such as a ranking or rating. For example, the feedback pane 702 may request a ranking or rating of the image quality of an image reconstruction.

The above-described interfaces and tools may be provided as an integrated component of an image reconstruction or scanner control workstation. For example, the interfaces and tools may be integrated with or provided by the e.soft image analysis software product and/or nuclear medicine workstation product from Siemens AG and/or Siemens Medical Solutions USA, Inc.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method of clinical collaboration between a clinical site and an analysis site, the method comprising:
   receiving scan data from a scanner via a first reconstruction computer system at the clinical site;
   implementing a reconstruction procedure on the received scan data using a second reconstruction computer system at the analysis site and configured in accordance with a reconstruction configuration parameter, the analysis site being remote from the clinical site; and
   transmitting data indicative of the reconstruction configuration parameter to the first reconstruction computer system to configure the first reconstruction computer system in accordance with the reconstruction configuration parameter;
   wherein the first and second reconstruction computer systems are configured to generate a reconstruction configuration interface to modify reconstruction parameter settings; and
   wherein implementing the reconstruction procedure comprises generating the reconstruction configuration interface at the second reconstruction computer system to establish the reconstruction configuration parameter as one of the reconstruction parameter settings.

2. The method of claim 1, wherein transmitting the data indicative of the reconstruction configuration parameter comprises synchronizing reconstruction parameter settings of the first reconstruction computer system and the second reconstruction computer system.

3. The method of claim 1, further comprising configuring the reconstruction procedure via a reconstruction customization tool provided via the reconstruction configuration interface generated at the second reconstruction system.

4. The method of claim 1, wherein receiving the scan data comprises initiating a data synchronization between the first and second reconstruction computer systems such that the second reconstruction computer system is configured as a clone of the first reconstruction computer system.

5. The method of claim 1, wherein receiving the scan data comprises aggregating scan data from a plurality of reconstruction computer systems including the first reconstruction computer system and not disposed at the analysis site.

6. The method of claim 1, further comprising:
   rendering, with the second reconstruction computer system, an image generated by the reconstruction procedure; and
   sharing data representative of user feedback on the rendered image between the first and second reconstruction computer systems.

7. The method of claim 6, wherein rendering the image comprises generating a visualization interface configured to facilitate comparison of more than two reconstruction results and storage of feedback data for the comparison.

8. The method of claim 1, wherein the scan data is anonymized by the first reconstruction computer system before the scan data is received for implementing the reconstruction procedure.

9. The method of claim 1, wherein implementing the reconstruction procedure comprises batch processing of multiple scan data sets, batch processing of the scan data in accordance with multiple sets of reconstruction parameters, or a combination thereof.

10. The method of claim 1, wherein transmitting the data indicative of the reconstruction configuration parameter is implemented concurrently with implementing the reconstruction procedure.

11. A system to facilitate clinical collaboration with a clinical site, the system comprising:
   a memory in which data transfer instructions and reconstruction instructions are stored;
   a processor in communication with the memory and configured to execute the data transfer instructions to receive scan data from a scanner via a reconstruction computer system at the clinical site;
   wherein the processor is configured to execute the reconstruction instructions to implement a reconstruction procedure on the received scan data in accordance with a reconstruction configuration parameter;
   wherein the processor is further configured to execute the data transfer instructions to transmit data indicative of the reconstruction configuration parameter to the reconstruction computer system to configure the reconstruction computer system in accordance with the reconstruction configuration parameter;
   wherein the processor and the reconstruction computer system are further configured to execute the reconstruction instructions to generate a reconstruction configuration interface to modify reconstruction parameters settings; and
   wherein the processor is further configured to execute the reconstruction instructions to establish, via the reconstruction configuration interface, the reconstruction configuration parameter as one of the reconstruction parameter settings.

12. The system of claim 11, wherein the processor is further configured to execute the data transfer instructions to synchronize reconstruction parameter settings of the reconstruction computer system and the system.

13. The system of claim 11, wherein the processor is further configured to execute the reconstruction instructions to provide a reconstruction customization tool via the reconstruction configuration interface.

14. The system of claim 11, wherein the processor is further configured to execute the data transfer instructions to aggregate scan data from a plurality of scanner site reconstruction computer systems including the reconstruction computer system.

15. The system of claim 11, wherein the processor is further configured to execute the reconstruction instructions to generate a visualization interface configured to facilitate comparison of more than two reconstruction results and storage of feedback data for the comparison.

16. The system of claim 11, wherein the processor is further configured to execute the reconstruction instructions to batch process multiple scan data sets, batch process the scan data in accordance with multiple sets of reconstruction parameters, or a combination thereof.

17. A computer program product to facilitate clinical collaboration between a clinical site and an analysis site, the computer program product comprising one or more non-transitory computer-readable storage media having stored thereon computer-executable instructions that, when executed by one or more processors of a computing system, cause the computing system to perform the method, the method comprising:
  anonymizing scan data captured by a scanner and received via a scanner control workstation at the clinical site after image registration of the scan data by the scanner control workstation;
  transferring the anonymized scan data to a reconstruction computer system at the analysis site;
  receiving a reconstruction configuration parameter from the reconstruction computer system to configure a reconstruction procedure;
  generating a reconstruction configuration interface to modify reconstruction parameter settings of the reconstruction procedure; and
  configuring the reconstruction procedure with a further reconstruction configuration parameter as one of the reconstruction parameter settings via a reconstruction customization tool provided via the reconstruction configuration interface;
  wherein the reconstruction computer system at the analysis site is configured to generate the reconstruction configuration interface to modify the reconstruction parameter settings at the reconstruction computer system and establish the reconstruction configuration parameter as one of the reconstruction parameter settings at the reconstruction computer system.

18. The computer program product of claim 17, wherein receiving the reconstruction configuration parameter comprises synchronizing reconstruction parameter settings with the reconstruction computer system.

19. The computer program product of claim 17, wherein the method further comprises rendering an image generated by the reconstruction procedure via a visualization interface, the visualization interface being configured to facilitate comparison of more than two reconstruction results and storage of feedback data for the comparison.

20. The computer program product of claim 17, wherein the method further comprises transferring the further reconstruction configuration parameter to the reconstruction computer system.

* * * * *